United States Patent [19]
Hum

[11] Patent Number: 5,657,498
[45] Date of Patent: Aug. 19, 1997

[54] METHODS AND APPARATUS FOR ACQUIRING TABLE ELEVATION INFORMATION

[75] Inventor: Russell Wayne Hum, Waukesha, Wis.

[73] Assignee: General Electric Company, Milwaukee, Wis.

[21] Appl. No.: 560,829

[22] Filed: Nov. 20, 1995

[51] Int. Cl.$^6$ ............................... A47B 9/16; A61B 6/04
[52] U.S. Cl. ................... 5/601; 108/147; 378/20
[58] Field of Search ........................ 5/600, 601, 611, 5/11; 378/20, 195, 196, 208, 209; 108/7, 50, 147

[56] References Cited

U.S. PATENT DOCUMENTS

| | | | |
|---|---|---|---|
| 4,315,466 | 2/1982 | Boerigter | 108/147 |
| 4,576,368 | 3/1986 | Ogawa et al. | |
| 4,583,242 | 4/1986 | Vinegar et al. | |
| 4,714,025 | 12/1987 | Wallin et al. | 108/147 |
| 4,914,682 | 4/1990 | Blumenthal | |
| 5,224,429 | 7/1993 | Borgman et al. | 108/147 |
| 5,490,296 | 2/1996 | Fleury et al. | 5/86.1 |
| 5,499,415 | 3/1996 | McKenna | 5/601 |

*Primary Examiner*—Darnell M. Boucher
*Assistant Examiner*—Robert G. Santos
*Attorney, Agent, or Firm*—John S. Beulick; John H. Pilarski

[57] ABSTRACT

Apparatus and methods for determining cradle support elevation in an imaging system are described. In one form, the apparatus includes a support rail secured to and between table support legs of a table arrangement. The support rail is maintained substantially parallel with the cradle support. An encoder, coupled to the support rail, generates signals indicative of the cradle support elevation. The encoder signals can be used to determine, using a linear function, cradle support elevation. More specifically, although the cradle support movements are non-linear, the cradle support elevation apparatus provide linear feedback which may be used to determine cradle support elevation.

18 Claims, 3 Drawing Sheets

METHODS AND APPARATUS FOR ACQUIRING TABLE ELEVATION INFORMATION

FIELD OF THE INVENTION

This invention relates generally to determining table elevation and more particularly, to methods and apparatus for determining patient elevation prior to performing a scan using an imaging system.

BACKGROUND OF THE INVENTION

When performing medical imaging, such as computed tomography imaging, it is important to know the location, or elevation, of the patient relative to the imaging machine prior to initiating the scan. Such information is important, for example, so that an accurate image can be reconstructed from the scan data.

In at least one known table apparatus used in an imaging system, the table apparatus includes a cradle support, a base, parallel table support legs, a driving mechanism, and an encoder. A cradle is located on the cradle support and is movable on the cradle support through the gantry. Each parallel table support leg has one end pivotally connected to the cradle support and the other, opposite, end pivotally connected to the base. The pivot connections are sometimes referred to hereinafter as pivot points. The cradle is maintained in a substantially horizontal position and is movable vertically and laterally relative to the base. The driving mechanism, which may be a hydraulic or electric actuator, has one end pivotally mounted to one of the table support legs and an opposite end pivotally mounted to the base.

The encoder is coupled to one of the support legs and, in operation, generates pulses indicative of the angular orientation (theta) of the support leg with respect to the base. The output of the encoder is coupled to a control processor which is programmed to control operation of the imaging machine.

In operation, the cradle support typically is initially located at a lower position. A patient lies on a cradle, located on the cradle support. The driving mechanism then drives, or pushes, the one leg support so that the cradle support and cradle move upward (vertically) and towards (laterally) the gantry. As the angular orientation of the legs changes, the encoder generates pulses indicative of such angular orientation.

The pulses, as explained above, are supplied to the control processor. The pulses may be store in an accumulator, and once the patient is positioned at the desired elevation, the accumulated pulse count is utilized to determine the elevation of the cradle support. Particularly, such elevation is determined by the processor using the following relationship:

$$Height = R * \sin(theta) + offset$$

where:

R is the attachment point of the cradle support (length of the table support leg);

theta is the angle supplied by the encoder; and offset is an adjustment for the base and cradle offsets from the pivot points.

To determine the patient elevation as explained above, processor firmware resources and time are required. Of course, it is desirable to limit the amount of such required resources and time. In addition, determining patient elevation in this manner is very sensitive to measurement errors and calculation roundoffs depending on the angle of elevation because the sensitivity of the encoder is high at higher elevations and low at lower elevations. Moreover, the relationship between encoder pulses, or counts, is non-linear in that such counts are not proportional to elevation. The non-linear nature of the elevation determination adds complexity to the elevation determination and increases the possibility for errors.

It is desirable, therefore, to reduce the processor resources and time required to determine cradle support elevation prior to a scan, and to utilize methods and apparatus which are not sensitive to measurement errors and calculation roundoffs depending on cradle elevation. It also is desirable to provide methods and apparatus which utilize linear relationships to determine cradle support elevation to simplify cradle support elevation determinations and further reduce the possibility for elevation determination errors.

SUMMARY OF THE INVENTION

These and other objects may be attained by elevation determination methods and apparatus which, in one embodiment of the apparatus, generates linear feedback data utilized to easily and quickly determine cradle support elevation. The elevation determination methods and apparatus may be used in a table arrangement which includes a base and a cradle support having parallel support legs coupled at opposite ends to, and extending between, the base and cradle support. The support legs are secured to the base and cradle support by pivot bearings so that the support legs are movable relative to the base and cradle support.

In accordance with one embodiment of the elevation determination apparatus, a support rail is pivotally attached to and extends between respective table support legs. The rail is substantially parallel to the cradle support and base. The apparatus further includes a substantially stationary member, which may be secured to the table arrangement, and a longitudinally slidable member secured to the stationary member. One end of the slidable member is attached to a roller located on the support rail. The other end of the slidable member is secured to a line from a spring loaded pulley attached to the table arrangement base. An encoder is coupled to the pulley and generates pulses corresponding to the length of line fed out from the pulley. The encoder is electrically coupled to the imaging system computer.

In operation, since the elevation of the cradle support is linearly related to the elevation of the support rail, the feedback information, or pulses, from the encoder can be utilized to determine, using a linear relationship, the cradle support elevation. More specifically, as the cradle support moves from an initial lower elevation to a final higher elevation, the slidable member also moves from an initial lower elevation to a final higher elevation. As the slidable member moves to the higher elevation, line is fed out from the pulley. The length of line fed out from the pulley can be determined from the number of pulses output by the encoder. The encoder pulse count may be accumulated in the system computer, and once the patient is located at the desired position, the cradle support elevation can be determined by the system computer using the linear relationship:

$$A = k * a,$$

where

A is the vertical elevation of the cradle support relative to its initial position, k is a predetermined, e.g., by mechanical ratio by placement of the vertical feedback support, constant, and is the vertical height of the horizontal encoder support rail relative to its initial position.

Using the apparatus and methods described above, and particularly since cradle support elevation is determined using a linear relationship, the required processor resources and time are reduced as compared to the known manner for determining cradle elevation. In addition, due to the linear nature of the elevation determination, the above described methods and apparatus are not as sensitive to measurement errors and calculation roundoffs. Further, since the cradle support elevation may be determined using a relatively simple linear relationship, the possibility for elevation determination errors is reduced.

DETAILED DESCRIPTION OF THE DRAWINGS

Figure 1:
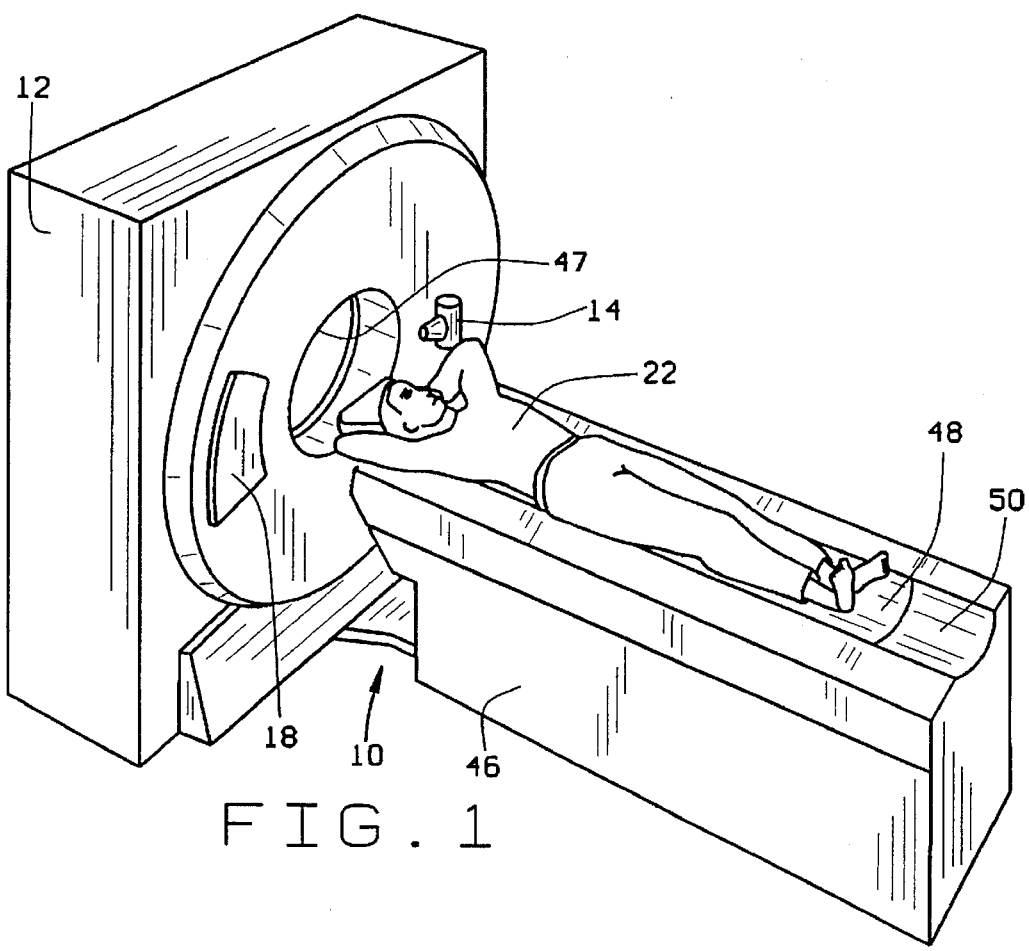
FIG. 1 is a pictorial view of a CT imaging system.
Figure 2:
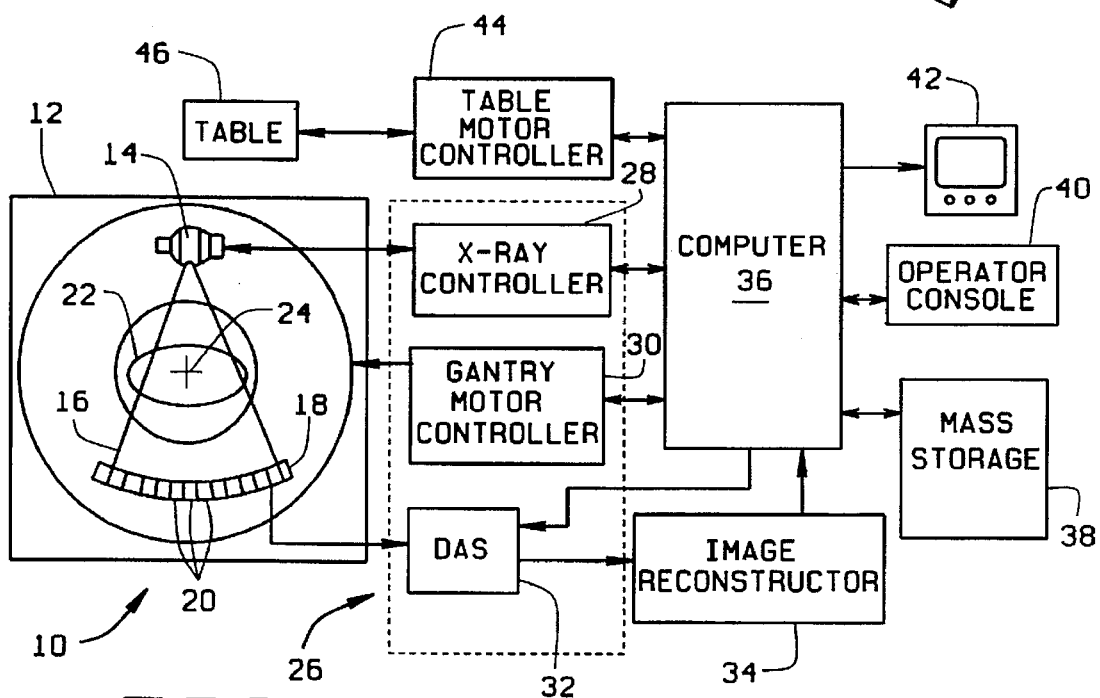
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Computer 36 receives commands and scanning parameters from an operator via console 40 that has a keyboard. An associated cathode ray tube display 42 allows the operator to observe the reconstructed image and other data from computer 36. Computer 36 operates a table motor controller 44 which controls a table arrangement 46 to position patient 22 in gantry 12. Particularly, table arrangement 46 moves portions of patient 22 through gantry opening 47. More specifically, table arrangement 46 includes a cradle 48 and a cradle support 50. Patient 22 lies on cradle 48 which is movable through gantry opening 47. Prior to scanning patient 22, it is important to know the elevation of cradle support 50 so that an accurate image from the scan data can be reconstructed.

The following discussion relates to methods and apparatus for determining cradle support elevation. Although such methods and apparatus sometimes are described in the context of CT system 10, it should be understood that such methods and apparatus are not limited to practice or use in connection with only CT systems. For example, it is contemplated that such methods and apparatus can be used in other imaging modalities such as in magnetic resonance, PET, nuclear and x-ray imaging machines.

Figure 3:
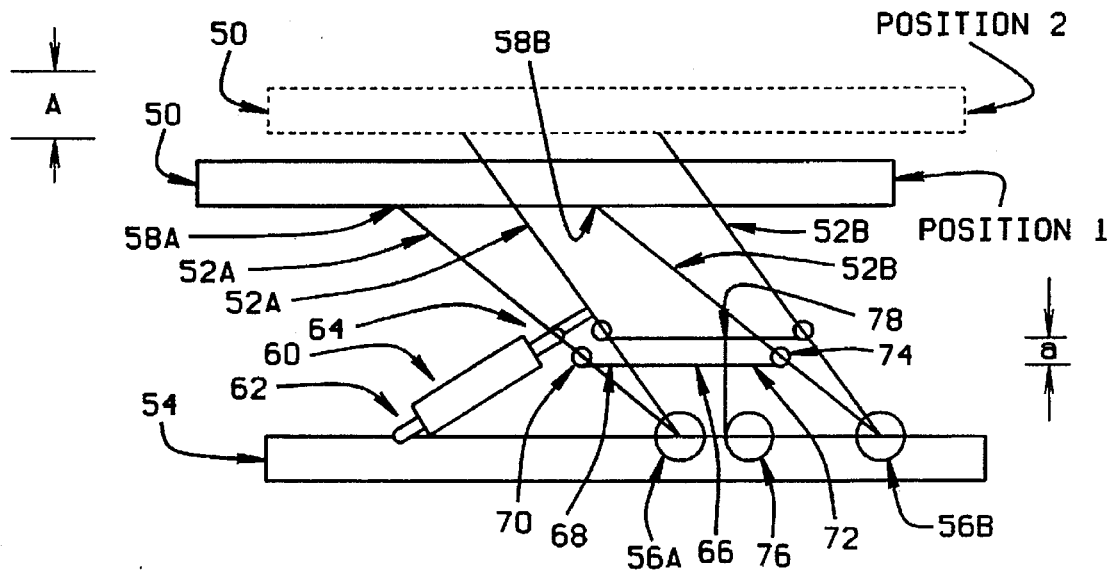
FIG. 3 is a schematic illustration of one embodiment of a table arrangement and an elevation determination apparatus in accordance with one embodiment of the present invention.

Referring specifically to FIG. 3, cradle support 50, support legs 52A and 52B, and a base 54 are schematically illustrated. Support legs 52A and 52B are pivotally mounted to base 54 by pivot bearings 56A and 56B, respectively. Legs 52A and 52B also are pivotally mounted, by support bearings 58A and 58B, to cradle support 50. Legs 52A and 52B are substantially parallel and although such legs 52A and 52B are pivotable with respect to base 54 and support 50, such legs 52A and 52B are maintained substantially parallel to each other. A driving mechanism 60 has a base end 62 mounted to base 54 and an extendable leg end 64 connected to table support leg 52A. Driving mechanism 60 may be a hydraulic or an electric actuator operable as described hereinafter in more detail.

The above described table assembly, which includes cradle support 50, support legs 52A and 52B, and base 54, is well known in the art. Such table assembly is particularly advantageous since as the cradle support elevation is increased, cradle support 50 also moves laterally with respect to base 54 and closer to the gantry (not shown). As explained above, however, known methods and apparatus for determining the elevation of cradle support 50 have certain shortcomings and disadvantages.

To overcome these shortcomings and disadvantages, and referring again to FIG. 3, an elevation determination apparatus in accordance with one embodiment of the present invention is shown schematically and includes a support rail 66 pivotally attached at one end 68 to leg 52A by a first rail pivot bearing 70 and at its other end 72 to leg 52B by a second rail pivot bearing 74. Support rail 66 is substantially parallel to cradle support 50 and base 54.

As shown schematically in FIG. 3, a spring loaded pulley 76 is secured to base 54 and a line extends from pulley 76 to support rail 66 as generally indicated at 78. Support rail 66 is slidably connected to the pulley line so that the pulley line is maintained substantially vertical with respect to base 54 and cradle support 50. A signal generator, such as an encoder, is coupled to pulley 76. The signal generator, in operation, generates pulses indicative of the length of the pulley line fed out by pulley 76, as described hereinafter in more detail. The signal generator also is electrically coupled to computer 36 (FIG. 2).

In an initial position, driving mechanism 60 is fully retracted, illustrated as Position 1 in FIG. 3. After placing a patient 22 or other object of interest on cradle support 50, driving mechanism 60 drives, or forces, leg 52A upward and laterally. Cradle support 50, having the cradle and patient thereon, is raised until the patient is at the desired location, such as at Position 2 shown in phantom in FIG. 3. As shown in FIG. 3, the extension of driving mechanism 60 causes cradle support 50 to move both vertically and laterally relative to base 54.

As cradle support 50 moves from Position 1 to Position 2, line is fed out from pulley 76. Also, support rail 66 slides longitudinally with respect to such pulley line so that the line remains in a substantially vertical orientation. As the line is fed out from pulley 76, the signal generator generates signals, or pulses, indicative of the length of line fed out.

Since the elevation of cradle support 50 is linearly related to the elevation of support rail 66, the feedback signals, or pulses, from the signal generator, can be utilized to determine, using a linear relationship, the elevation of cradle support 50. More specifically, if the signal generator is a pulse generating encoder in which each pulse corresponds to a predetermined length of line, an encoder pulse count may be accumulated in system computer 36. Once the patient is located at the desired position, the cradle support elevation can be determined by computer 36 using the linear relationship:

$$A = k * a,$$

where

A is the vertical elevation of the cradle support relative to its initial position, k is a predetermined, e.g., by mechanical ratio by placement of the vertical feedback support, constant, and a is the vertical height of the horizontal support rail relative to its initial position.

Using the apparatus and method described above, and particularly since cradle support elevation is determined using a linear relationship, the required computer resources and time are reduced as compared to the known manner for determining cradle elevation. In addition, due to the linear nature of the elevation determination, the above described method and apparatus are not as sensitive to measurement errors and calculation roundoffs. Further, since the cradle support elevation may be determined using a relatively simple linear relationship, the possibility for elevation determination errors is reduced.

Figure 4:
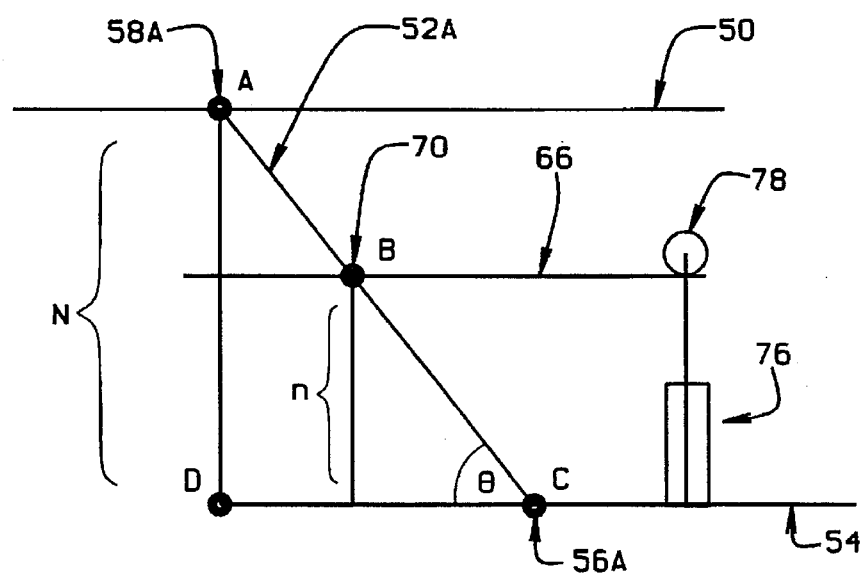
FIG. 4 is a schematic illustration of operation of the apparatus shown in FIG. 3.

FIG. 4 is a schematic illustration showing the angular relationship between support leg 52A and base 54. The angular relationships set forth below for support leg 52A also are applicable to support leg 52B. When support leg 52A is positioned at an angle (θ) with respect to base 54, then:

$$\mathrm{Sin}(\theta) = N/AC = n/BC$$

where

AC=length of support leg 52A;

BC=length of support leg 52A between rail pivot point 70 and pivot point 56A;

N=vertical distance between the cradle support 50 and base 54; and n=vertical distance between support rail 66 and base 54.

Vertical distance N between cradle support 50 and base 54 can be determined by:

$$N = K*n$$

where

K=length of support leg 52A divided by the length of support leg 52A between rail pivot point 70 and pivot point 56A.

K is thus a constant because the length of support leg 52A and the distance between first rail pivot point 70 and pivot point 56A is constant. Therefore, N is linearly related to n. Vertical distance n between support raft 66 and base 54 is determined based on signals generated by the signal generator coupled to pulley 76.

Figure 5:
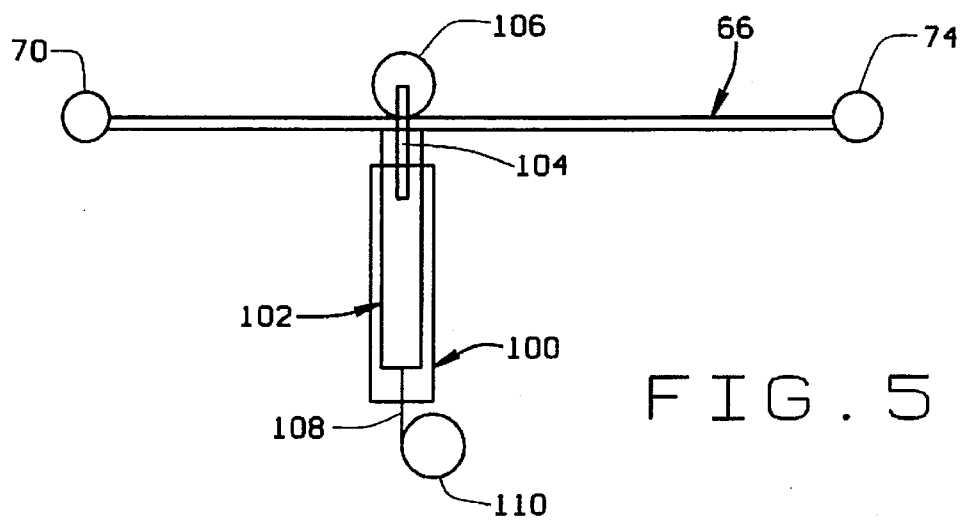
FIG. 5 is a side elevation view of one embodiment of an elevation determination apparatus in accordance with the present invention.

Referring to FIG. 5, one embodiment of an elevation determination apparatus in accordance with the present invention is illustrated. More particularly, the apparatus includes support rail 66 pivotally attached, by pivot bearings 70 and 74, to respective table support legs (not shown). The apparatus further includes a support rail elevation apparatus which has a substantially stationary member 100, which may be secured to the table arrangement, and a longitudinally slidable member 102 slidably secured to stationary member 100. One end of slidable member 102 is attached, via an extension 104, to a roller 106 positioned on support rail 66. The other end of slidable member 102 is secured to a line 108 from a spring loaded pulley 110 attached to the table arrangement base (not shown). An encoder (not shown) is coupled to pulley 110 and generates pulses indicative of the amount of line 108 fed out by pulley 110. The encoder is electrically coupled to the imaging system computer (not shown), and as described above, pulses from the encoder are utilized to determine cradle support elevation.

Figure 6:
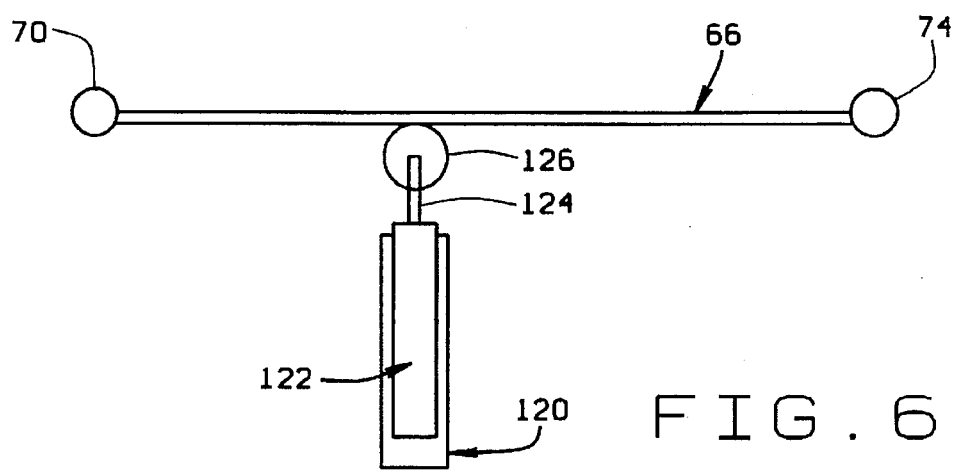
FIG. 6 is a side elevation view of another embodiment of an elevation determination apparatus in accordance with the present invention.

FIG. 6 illustrates a second embodiment of an elevation determination apparatus in accordance with the present invention. More particularly, the apparatus includes support rail 66 pivotally attached, by pivot bearings 70 and 74, to respective table support legs (not shown). The apparatus further includes a support rail elevation apparatus which has a substantially stationary member 120, which may be secured to the table arrangement, and a longitudinally slidable member 122 slidably secured to stationary member 120. One end of slidable member 122 is attached, via an extension 124, to a roller 126 which is in contact with a lower surface of support rail 66. A spring loaded linear encoder or a spring loaded linear potentiometer is connected to slidable member 122 and forces slidable member 122 towards support rail 66 so that roller 126 substantially remains in contact with rail 66. The encoder or potentiometer is electrically coupled to the imaging system computer (not shown), and signals from the encoder or potentiometer are utilized to determine cradle support elevation.

Figure 7:
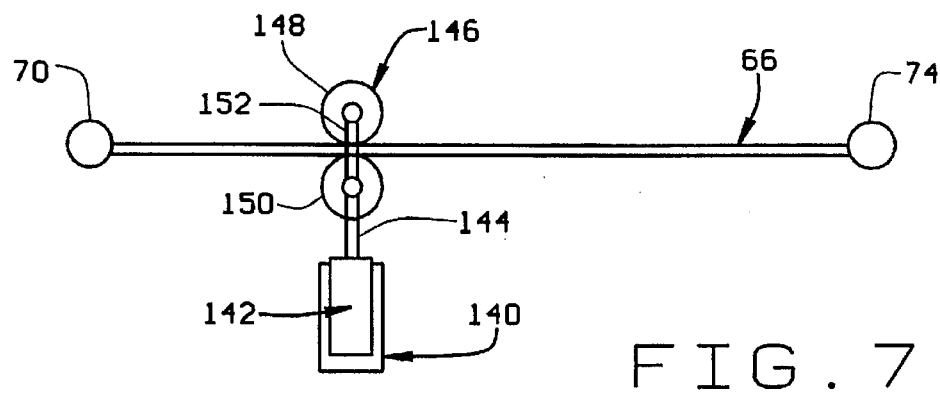
FIG. 7 is a side elevation view of yet another embodiment of an elevation determination apparatus in accordance with the present invention.

A third embodiment of an elevation determination apparatus in accordance with the present invention is illustrated in FIG. 7. More particularly, the apparatus includes support rail 66 pivotally attached, by pivot bearings 70 and 74, to respective table support legs (not shown). The apparatus further includes a support rail elevation apparatus which has a substantially stationary member 140, which may be secured to the table arrangement, and a longitudinally slidable member 142 slidably secured to stationary member 140. One end of slidable member 142 is attached, via an extension 144, to a double cam arrangement 146 which includes two rollers 148 and 150 coupled together by a brace 152 and in contact with lower and upper surfaces, respectively, of support rail 66. A linear encoder or a linear potentiometer is connected to slidable member 142 and is electrically coupled to the imaging system computer (not shown). In this embodiment, the encoder or potentiometer is not spring loaded. Signals from the encoder or potentiometer are utilized to determine cradle support elevation.

Many other embodiments of the elevation determination apparatus are possible. For example, signal generators other than encoders and potentiometers may be used, such as a resolver or an inductsyns. In addition, if an encoder is used, the encoder may be an incremental encoder or an absolute encoder. Such apparatus are well known and commercially available. In addition, although the elevation determination apparatus and methods are described above in an imaging system context, such apparatus and methods can be used in many other contexts, such as in a manufacturing setting to determine process table elevation. Rather than determining cradle support elevation, in such a context, the table top elevation may be determined.

Further, in some embodiments described above, the subject encoders and potentiometers are described as being oriented relative to, or coupled to, base 56. Such encoder and potentiometers, or other elevation determination apparatus, could, however, be oriented relative to, or coupled to, movable cradle support 50. Such a configuration also enables generating linear feedback with respect to a non-linearly moving cradle support 50.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. Apparatus for determining the elevation of a cradle support of a patient table for an imaging system, the table including at least a first and a second table support leg pivotally connected at a first end to a base and pivotally connected at a second end to the cradle support, a driving mechanism connected at one end to the base and at another end to at least one support leg, the driving mechanism configured to move the support legs with respect to the base to cause concurrent vertical and lateral movement of the cradle support while maintaining the cradle support substantially parallel to the base, said apparatus comprising:

at least one support rail for attaching at a first end to the first support leg and for attaching at a second end to the second support leg; and a support rail elevation determining apparatus slidably coupled to said support rail so that said support rail may move laterally with respect to said support rail elevation determining apparatus, said support rail elevation determining apparatus comprising a signal generator configured to generate signals indicative of the elevation of the cradle support.

2. Apparatus in accordance with claim 1 wherein the imaging system further includes a computer, said signal generator electrically coupled to the computer to provide the elevation indicative signals thereto.

3. Apparatus in accordance with claim 2 wherein the computer is programmed to determine cradle support elevation by:

$$N=K*n$$

where

N is the vertical distance between the cradle support and base,

K is a predetermined constant, and n is the vertical distance between said support rail and base.

4. Apparatus in accordance with claim 3 wherein said first end of said support raft is attached to the first support leg at a first pivot point and said second end of said support rail is attached to the second support leg at a second point and K is the length of the first support leg divided by the length of the first support leg between the first pivot point and the base.

5. Apparatus in accordance with claim 1 wherein said support rail elevation determining apparatus comprises a spring loaded pulley and a pulley line.

6. Apparatus in accordance with claim 5 wherein said signal generator is coupled to said pulley.

7. An apparatus in accordance with claim 5 wherein said support rail elevation apparatus further comprises:

a roller located on an upper surface of said support rail;

a substantially stationary member;

a longitudinally slidable member having first and second ends, said slidable member slidably secured to the substantially stationary member, said first end of the slidable member attached to said pulley line; and an extension having a first and a second end, said first end of said extension connected to said roller and said second end of said extension connected to said second end of said slidable member.

8. Apparatus in accordance with claim 1 wherein said signal generator is a linear encoder and said support rail elevation apparatus further comprises:

a roller positioned against a first surface of said support rail;

a substantially stationary member;

a longitudinally slidable member having first and second ends, said slidable member slidably secured to the substantially stationary member, said linear encoder being coupled to said slidable member; and an extension having a first and a second end, said first end of said extension connected to said roller and said second end of said extension connected to said second end of said slidable member.

9. Apparatus in accordance with claim 1 wherein said signal generator is a linear encoder and said supports rail elevation apparatus further comprises:

a double cam including a first roller and a second roller, said first roller positioned on a first surface of said support rail and said second roller positioned against a second surface of said support rail;

a substantially stationary member;

a longitudinally slidable member having first and second ends, said slidable member slidably secured to the substantially stationary member, said linear encoder being coupled to said slidable member; and an extension having a first and a second end, said first end of said extension connected to said roller and said second end of said extension connected to said second end of said slidable member.

10. Apparatus in accordance with claim 1 wherein said signal generator is an incremental encoder.

11. Apparatus in accordance with claim 1 wherein said signal generator is an absolute encoder.

12. Apparatus in accordance with claim 1 wherein said signal generator is potentiometer.

13. Apparatus in accordance with claim 1 wherein said signal generator is a resolver.

14. A method for determining the elevation of a cradle support of a patient table for an imaging system, at least first and second table support legs pivotally connected at a first end to a base and pivotally connected at a second end to the cradle support, a driving mechanism connected at one end to the base and at another end to at least one support leg, the driving mechanism configured to move the support legs with respect to the base to cause concurrent vertical and lateral movement of the cradle support while maintaining the cradle support substantially parallel to the base, at least one support rail attached at a first end to the first support leg and attached at a second end to the second support leg so that the support rail is substantially parallel to the cradle support and to the base, apparatus for determining the elevation of the support rail, the support rail elevation determining apparatus comprising a signal generator configured to generate signals indicative of the elevation of the cradle support, said method comprising:

acquiring signals from the signal generator indicative of the elevation of the cradle support; and determining the elevation of the support cradle using the acquired signals and a linear algorithm, the linear algorithm being:

$$N = K * n$$

where

N is the vertical distance between the cradle support and base,

K is a predetermined constant, and n is the vertical distance between the support rail and base.

15. An elevation determination apparatus for determining the elevation of a table top, at least first and second table support legs pivotally connected at a first end to a base and pivotally connected at a second end to the table, a driving mechanism connected at one end to the base and at another end to at least one support leg, the driving mechanism configured to move the support legs with respect to the base to cause concurrent vertical and lateral movement of the table top while maintaining the table top substantially parallel to the base, said apparatus comprising:

a support rail for pivotally attaching to and extending between respective table support legs;

a substantially stationary member;

a longitudinally slidable member slidably secured to said stationary member;

a roller configured to be located, and roll, on a surface of said support rail; and an extension member extending between and coupled at opposite ends to said roller and said slidable member.

16. An elevation determination apparatus in accordance with claim 15 further comprising a spring loaded pulley secured to the base, a line of said spring loaded pulley attached to said slidable member, a signal generator coupled to said pulley and configured to generate pulses indicative of the amount of line extending between said pulley and said slidable member.

17. An elevation determination apparatus in accordance with claim 15 further comprising a spring loaded pulley secured to the table, a line of said spring loaded pulley attached to said slidable member, a signal generator coupled to said pulley and configured to generate pulses indicative of the amount of line extending between said pulley and said slidable member.

18. An elevation determination apparatus in accordance with claim 15 wherein the table top elevation is determined using the linear relationship:

$$A = k * a,$$

where

A is the vertical elevation of the table top relative to its initial position, k is a predetermined constant, and a is the vertical elevation of said support rail relative to its initial position.

* * * * *